(12) United States Patent
Luinge et al.

(10) Patent No.: US 8,165,844 B2
(45) Date of Patent: Apr. 24, 2012

(54) MOTION TRACKING SYSTEM

(75) Inventors: Henk J Luinge, Enschede (NL); Daniel Roetenberg, Enschede (NL); Per J Slycke, Deventer (NL)

(73) Assignee: Xsens Holding B.V., Enschede (NL)

( * ) Notice: Subject to any disclaimer, the term of this patent is extended or adjusted under 35 U.S.C. 154(b) by 522 days.

(21) Appl. No.: 11/748,963

(22) Filed: May 15, 2007

(65) Prior Publication Data

US 2008/0285805 A1 Nov. 20, 2008

(30) Foreign Application Priority Data

Mar. 15, 2007 (EP) .................................... 07104283

(51) Int. Cl.
*A61B 5/103* (2006.01)
(52) U.S. Cl. ........ 702/152; 702/150; 702/151; 702/153; 600/543; 600/587; 382/107; 382/128
(58) Field of Classification Search .......... 702/150–153, 702/190; 600/543, 587; 382/107, 128
See application file for complete search history.

(56) References Cited

U.S. PATENT DOCUMENTS

| | | | |
|---|---|---|---|
| 4,106,094 A | 8/1978 | Land | |
| 5,645,077 A | 7/1997 | Foxlin | |
| 5,744,953 A | 4/1998 | Hansen | |
| 6,361,507 B1 | 3/2002 | Foxlin | |
| 6,474,159 B1 | 11/2002 | Foxlin et al. | |
| 6,691,074 B1 * | 2/2004 | Moriya et al. | 702/190 |
| 6,820,025 B2 * | 11/2004 | Bachmann et al. | 702/94 |

FOREIGN PATENT DOCUMENTS

| | | |
|---|---|---|
| NL | 07104283 | 3/2007 |
| NL | 1030440 | 5/2007 |
| WO | PCT/NL2006/000572 | 5/2007 |

OTHER PUBLICATIONS

Yun et al. "Self-Contained Posiiton Tracking of Human Movement Using Small Inertial/Magnetic Sensor Modules," Apr. 10-14, 2007.*
U.S. Appl. No. 12/049,019, Luinge et al.
U.S. Appl. No. 12/093,914, Slycke et al.
Product Brochure entitled Moven by Xsens, Innovator in Inertial Sensor Technology, Copyright 2007, pp. 1-3.
International Search Report, pp. 1-10.

(Continued)

*Primary Examiner* — Sujoy Kundu
(74) *Attorney, Agent, or Firm* — Miller, Matthias & Hull LLP

(57) ABSTRACT

A system is provided for capturing motion of a moving object via a plurality of motion sensor modules placed on various body segments. The sensor modules capture both 3D position and 3D orientation data relating to their respective body segments, thereby gathering motion data having six degrees of freedom with respect to a coordinate system not fixed to the body. Each body sensor collects 3D inertial sensor data and, optionally, magnetic field data. In embodiments, either DSP circuitry within the sensor modules or an external computing device, processes the sensor data to arrive at orientation and position estimates by using an estimation algorithm, such as a Kalman filter or a particle filter. The processing includes biomechanical model constraints that allow flexibility in the joints and provide characteristics for various joint types. To improve estimation accuracy, the system may be integrated with various types of aiding sensors.

15 Claims, 9 Drawing Sheets

OTHER PUBLICATIONS

Roetenberg D., Inertial and Magnetic Sensing of Human Motion, Ph.D. thesis, Universtity of Twente, obtained from the Internet on Jun. 9, 2008 at http://www.xsens.com/Static/Documents/UserUpload/papers/Inertial%20and%20Magnetic%20Sensing%20of%20Human%20Motion.pdf, Copyright 2006, pp. 1-128.

Luinge H.J., Inertial Sensing of Human Movement, Ph.D. thesis, University of Twente, obtained from the Internet on Jun. 9, 2008 at http://www.xsens.com/Static/Documents/UserUpload/papers/Inertial_Sensing_of_Human_Movement_Thesis Luinge.pdf, , Copyright 2002, pp. 1-88.

Cooper, G. et al., Inertial sensor-based knee flexion/extension angle estimation, *Journal of Biomechanics* 42 (2009) pp. 2678-2685.

* cited by examiner

MOTION TRACKING SYSTEM

CROSS-REFERENCE TO RELATED APPLICATIONS

This patent application is related to International Patent Application No. PCT/NL2006/000572, filed Nov. 15, 2006 and claims the benefit under 35 U.S.C. 119(a) of European Patent Application No. EP07104283, filed Mar. 15, 2007, all of which are incorporated herein by reference in their entirety.

FIELD OF THE INVENTION

This invention relates generally to the field of motion analysis and more specifically to modeling and tracking the motion of an object with a plurality of sensors.

BACKGROUND OF THE INVENTION

Many different disciplines use motion analysis systems to capture movements and postures of the human body. To make realistic animations for movies and computer games, movements of the actor are captured and mapped on a character. In sports, motion analysis techniques are used to analyze and improve performances. In the field of medicine and rehabilitation, recordings of human motion can be used, for example, to evaluate gait patterns.

Motion capture is often performed using magnetic or camera-based systems. In camera-based systems, reflective or light-emitting markers attached to the body are observed by a number of cameras from which the 3D position can be reconstructed using triangulation of each camera 2D image. With magnetic trackers, magnetic sensors measure the field as emitted by a source placed near the subject from which position and orientation of the sensor with respect to the source can be calculated. The set-up of external emitters or cameras limits the working volume where the subject can be captured and impedes many applications. Besides this major limitation and high costs, optical systems suffer from occlusion and reflection problems and magnetic trackers are easily disturbed by metallic objects in the vicinity.

To capture human body movements and postures without the need for external emitters or cameras several other systems are available. Mechanical trackers utilize rigid or flexible goniometers which are worn by the user. These angle measuring devices provide joint angle data to kinematic algorithms which are used to determine body posture. Attachment of the body-based linkages as well as the positioning of the goniometers present several problems. The soft tissue of the body allows the position of the linkages relative to the body to change as motion occurs. Even without these changes, alignment of the goniometer with body joints is difficult. This is specifically true for multiple degree of freedom (DOF) joints, like the shoulder.

U.S. Pat. Nos. 6,820,025 to Bachmann et al. and 5,645,077 to Foxlin, as well as Luinge H. J., "Inertial Sensing of Human Movement," Ph.D. thesis, University of Twente (2002), describe the use of miniature inertial and magnetic sensor modules to measure body segment orientation. These sensors measure the motion of the segment on which they are attached, independently of other system with respect to an earth-fixed reference system. They consist of gyroscopes, which measure angular velocities, accelerometers, which measure accelerations including gravity, and magnetometers measuring the earth magnetic field. When it is known to which body segment a sensor is attached, and when the orientation of the sensor with respect to the segments and joints is known, the orientation of the segments can be expressed in the global frame. By using the calculated orientations of individual body segments and the knowledge about the segment lengths, orientation between segments can be estimated and a position of the segments can be derived under strict assumptions of a linked kinematic chain (articulated model). This method is well-known in the art and assumes an articulated rigid body in which the joints only have rotational degrees of freedom, as described in Bachmann.

In such an approach of adding up vectors of different orientation, orientation errors, calibration errors and joint model errors accumulate as position errors in the connecting body parts. In fact, a human body and its joints can not be modeled as a pure kinematic chain with well-defined joints like hinge-joints and ball-and-socket-joints. Each human joint allows some laxity in all directions (both position and orientation) other than its main direction of movement. Further, to be able to track complex human joints and non-rigid body parts such as the back and shoulder accurately, more than three degrees of freedom, as given by an orientation measurement, are required. Furthermore, importantly, with only orientation driven motion capture, it is not possible to analyze the clearance of both feet, which occurs during running or jumping. Using this approach, it is also not possible to accurately determine the displacement of the body with respect to a coordinate system not fixed to the body.

The sensor modules should be attached tightly with respect to the bones. However, during use of the motion capture system, sensors can move with respect to the bone. This is caused by the elastic properties of the skin, fat and muscle contractions. These soft tissue artifacts are also present in other motion tracking systems and will introduce significant errors.

BRIEF SUMMARY OF THE INVENTION

Embodiments of the invention are used to provide a system for capturing motion of a moving animate object, such as a human body, via a body suit having a plurality of sensor modules placed on various body segments. In other embodiments, the sensor modules are not associated with a body suit, in which case the sensor modules are strapped down, taped, or otherwise individually affixed to the object's body. The sensor modules capture signals for estimating both three-dimensional (3D) position and 3D orientation data relating to their respective body segments, thereby gathering motion data having six degrees of freedom with respect to a coordinate system not fixed to the body. Each body sensor collects 3D inertial sensor data, such as via accelerometers and gyroscopes, and, optionally, magnetic field data via magnetometers. To provide a six-degree-of-freedom tracking of each body segment having one or more sensor modules, each body segment's orientation and position are estimated by, respectively, integrating the gyroscope data and double integrating the accelerometer data in time. In embodiments, either internal digital signal processing (DSP) circuitry within the body sensors or an external computing device, such as a computer or a microcontroller, processes the sensor data via a sensor fusion circuit to arrive at orientation and position estimates by using an estimation algorithm, such as a Kalman filter or a particle filter.

Over time, integration of inertial sensor data, including acceleration and angular velocity, leads to drift errors due to presence of sensor noise, sensor signal offset, or sensor orientation error. To correct the estimated quantities, such as orientation, velocity, or position, the sensor fusion circuit updates the estimates at predetermined time intervals. Further, the processing of the inertial sensor data from the body sensors includes constraints based on biomechanical characteristics of the body, such as a human body, detection of contact points of the body with an external world, and, optionally, the presence of a gravity field. Other embodiments of the system are used for tracking the motion of an inanimate object, such as a robot. In this case, the processing of inertial sensor data employs the corresponding mechanical constraints specific to the inanimate object.

The biomechanical constraints comprise a biomechanical model which assumes that a subject's body includes body segments linked by joints and that the sensors are attached to the subject's body segments. Hence, the sensor readings are correlated according to the biomechanical model that allows some laxity in the joints and provides for different biomechanical characteristics for various joint types. For example, knee and shoulder joints are assigned different biomechanical constraints. The biomechanical model allows a higher level of accuracy in estimating body motion. Integration of all measured accelerations allows tracking of all types of movements, including jumping and displacements in space with respect to a starting point. Due to the flexibility of the constraints, the actual movement that is captured does not necessarily describe a strict or rigid articulated body. Therefore, elements like jumping and moving in irregular terrain, such as stair climbing, are accurately recorded. As a further advantage, the system allows capturing, via inertial sensing, the movement of e.g., a shoulder, which does not behave as a strict joint.

To improve the accuracy of captured motion data or to reference to an external co-ordinate system, for example in estimating the position of the entire body in space, embodiments of the system are integrated with various types of aiding sensors, such as magnetic sensors, GPS, RF-based local positioning sensors, a barometer, a camera, as well as pressure and/or force sensors.

BRIEF DESCRIPTION OF THE DRAWINGS

While the appended claims set forth the features of the present invention with particularity, the invention and its advantages are best understood from the following detailed description taken in conjunction with the accompanying drawings, of which:

DETAILED DESCRIPTION OF THE INVENTION

The following examples further illustrate the invention but, of course, should not be construed as in any way limiting its scope.

Figure 1:
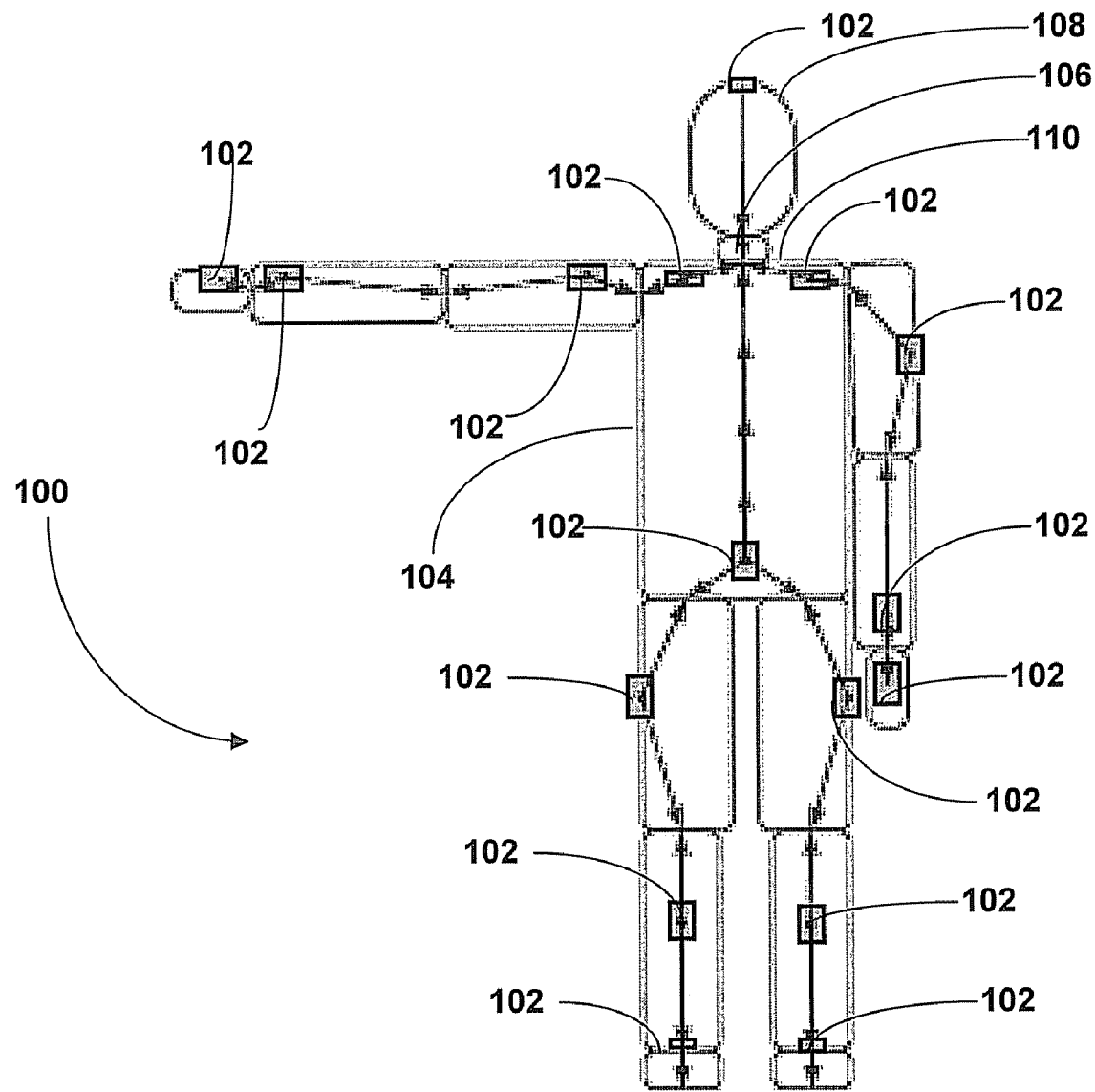
FIG. 1 is a schematic diagram of a body suit having a plurality of inertial sensors for tracking the motion of a moving body, as contemplated by an embodiment of the invention.

Turning to FIG. 1, an implementation of a system contemplated by an embodiment of the invention is shown with reference to a body suit 100 having a plurality of sensor modules 102 placed on various body segments, such as an object's head, torso, arms, legs, etc. Preferably, the body suit 100 is a human body suit for collecting motion data from a human being; however other embodiments include animal body suits for collecting animal motion data. In yet another embodiment, the sensor modules 102 are not associated with a body suit. In this case, the sensor modules are strapped down, taped, or otherwise individually affixed to the object's body segments. The sensor modules 102 capture both three-dimensional (3D) position and 3D orientation data relating to their respective body segments, thereby gathering motion data having six degrees of freedom with respect to a coordinate system not fixed to the body 104. Each body sensor 102 collects 3D inertial sensor data, such as via accelerometers and gyroscopes, and, optionally, magnetic field data via magnetometers. To provide a six-degree-of-freedom tracking of each body segment having one or more motion sensor modules 102, each body segment's orientation and position are estimated by, respectively, integrating the gyroscope data and double integrating the accelerometer data in time. The orientation and position estimates are obtained using a Strapdown Inertial Navigation System (INS) approach illustrated in FIG. 2 and further described in A. Gelb, "Optimal Estimation," MIT Press (1974), which is incorporated by reference in its entirety herein for everything that it teaches.

Figure 2:
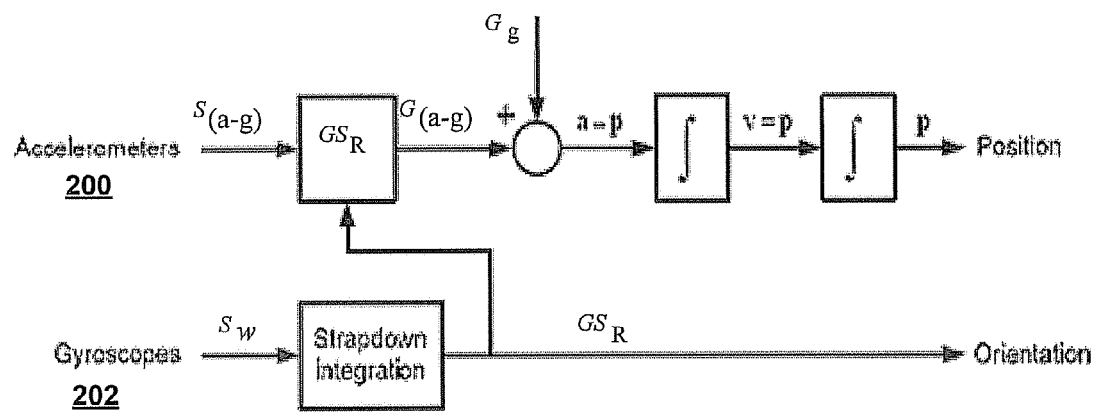
FIG. 2 is a schematic diagram illustrating the calculation of position and orientation information using accelerometer and gyroscope data collected by inertial sensors of FIG. 1, in accordance with an embodiment of the invention.

FIG. 2 illustrates a simplified Inertial Navigation System, in which certain parameters, such as the earth rotation (which can be measured with the gyroscopes), are neglected. Using very accurate sensors, this constant earth rate can be taken into account. Linear accelerometers 200 measure the vector sum of acceleration a and gravitational acceleration g in sensor coordinates. To calculate the displacement of the sensor by integration of the acceleration, the component of gravity must be removed. For this, the orientation of the accelerometer with respect to the vertical needs to be known. To measure the orientation, a gyroscope 202 is used. The gyroscope 202 measures angular velocity, and if integrated over time provides the change in angle with respect to an initially known angle. After removing the gravity component, the acceleration a can be integrated once to velocity v and twice to position p. In embodiments, either internal digital signal processing (DSP) circuitry within each sensor module 102 or an external computing device, such as a microcontroller, processes the sensor data to arrive at orientation and position estimates.

Over time, integration of inertial sensor data, including acceleration and angular velocity, leads to drift errors due to presence of sensor noise, sensor signal offset, or sensor orientation error. Therefore, it is necessary to correct the estimated quantities such as orientation, velocity, or position, at frequent time intervals. Corrections of these quantities are achieved by performing measurement updates and utilizing constraints or assumptions for sensor data processing. Specifically, the processing of the inertial sensor data from sensors 102 further includes constraints based on biomechanical characteristics of a human body, contact points of the body with an external world, and, optionally, aiding sensors. The external contact points are an intersection of the mesh model of the body with a mesh model of the world. The biomechanical model can be extended to a representation of a shape with or without non-human shapes such as shoes or walking aids. The intersection can be assigned several physical properties such as friction.

The biomechanical constraints comprise a biomechanical model which assumes that a subject's body includes body segments linked by joints and that the sensor modules 102 are attached to the subject's body segments. Hence, the sensor readings are correlated according to the biomechanical model that allows some laxity in the joints and provides for different biomechanical characteristics for various joint types. For example, the biomechanical model uses different constraints for the knee and shoulder joints. Therefore, the biomechanical model allows a higher level of accuracy in estimating body motion. The biomechanical characteristics of various human joint types are described in V. M. Zatsiorsky, "Kinematics of Human Motion," Human Kinetics (1998), which is incorporated herein by reference in its entirety for everything that it teaches. In one embodiment, the biomechanical model represents 23 segments linked by 22 joints with corresponding joint properties. Other embodiments of the system are used for tracking the motion of an inanimate object, such as a robot or another mechanical object. In this case, the processing of inertial sensor data employs mechanical joint constraints corresponding to the specific motion characteristics of the object.

Furthermore, the integration of all measured accelerations allows tracking of all types of movements, including jumping, displacements in space with respect to a starting point, and moving in irregular terrain, such as stair climbing. By contrast, these movements cannot be captured when calculation of body kinematics uses only orientation information without taking into account the integrated acceleration data.

The assumptions about joints in an articulated body are used to limit the boundless F integration drift of each sensor, while the detection of external contacts is used to limit the boundless integration error of the complete assembled body model. Due to the flexibility of the biomechanical constraints, however, the actual movement that is captured does not merely describe a strict or rigid articulated body because it takes into account laxity of the joints. As a further advantage, the system allows capturing, via inertial sensing, the movement of a shoulder, which does not behave as a strict joint.

To improve the accuracy of captured motion data, for example in estimating the position of the entire body in space, embodiments of the system are integrated with various types of aiding sensors, such as magnetic sensors, GPS, RF-based local positioning sensors, a barometer, a camera, as well as pressure and/or force sensors.

Figure 3:
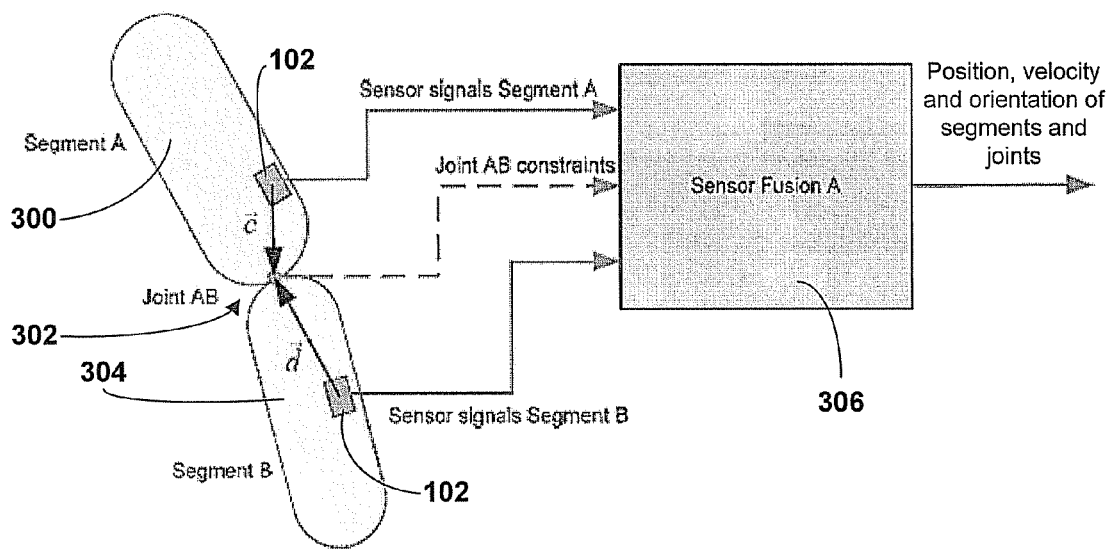
FIG. 3 is a schematic diagram illustrating a sensor fusion scheme for estimating the position, velocity, and orientation of segments and joints of a moving body of FIG. 1 by taking into account the joint constraints of connecting body segments.
Figure 4:
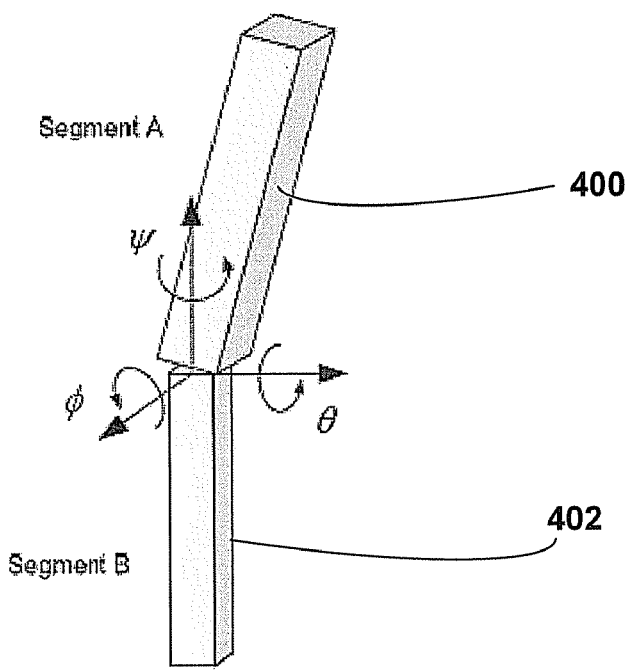
FIG. 4 is a schematic diagram illustrating three angles of rotation within a knee joint.
Figure 5:
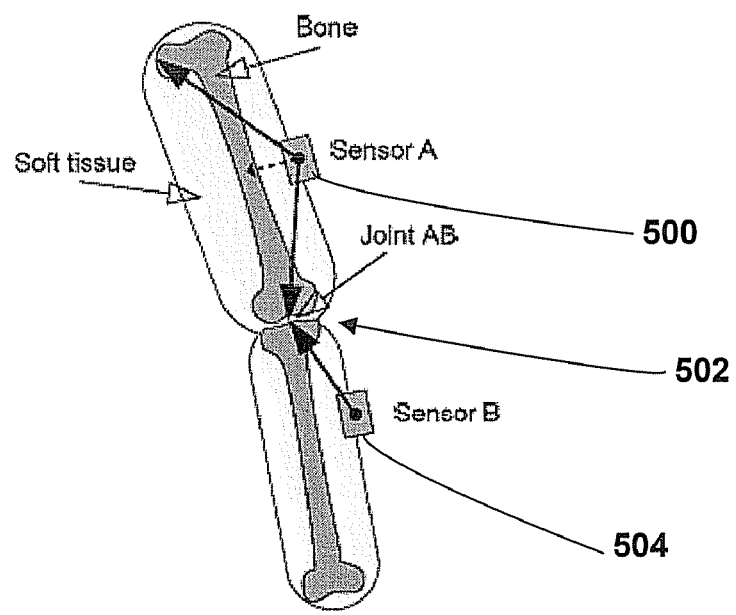
FIG. 5 is a schematic diagram illustrating a skin artifact that occurs when a sensor moves with respect to a bone of a given segment.

Turning to FIGS. 3-5, the operation of a biomechanical body model is illustrated in more detail. For position estimates, an essential constraint consists of a linked body segment model. As illustrated in FIG. 3, a sensor module 102 is attached to a body segment 300, with a known alignment between the sensor and its associated body segment. The sensor 102 is located at a vector position c from joint 302. On segment 304, a second sensor 102 is placed at vector position d from the joint 302. Thus, the joint 302 is described as a constraint in which vectors c and d are connected. This is not a rigid connection, however, since human and animal joints are not absolutely rigidly connected. Preferably, to reflect the natural flexibility of various types of body joints, the model includes statistical variations for each direction of motion in a given type of joint. For instance, hinge and ball-socket type joints include different restrictions of segment rotations, wherein each set of restrictions includes a range of statistically acceptable motion (e.g., ±n degrees). For example, as described in Zatsiorsky supra, statistical range of motion for a wrist joint is 5 degrees flexion, 30 degrees extension, and 15 degrees ulnar deviation. Similarly, typical translation of lower cervical spine joints is about 2.5 to 4.0 mm, while the occipital-oatlantal joint (spine) includes a flexion range of 13 degrees.

Furthermore, within a given joint, rotation of one segment with respect to another is often more restricted in one or more directions. In FIG. 4, in case of a knee joint, for example, the most dominant direction of rotation between upper leg (segment 400) and lower leg (segment 402) is flexion and extension $\Phi$, while internal/external rotation $\Psi$ and varus/valgus angles $\theta$ are often limited to only a few degrees.

Referring again to FIG. 3, using biomechanical modeling, the joint relation can be expressed as a linearized function: $y_t = Hx_t + v_t$, where $x_t$ is the state vector at time t, H is a matrix, $v_t$ is an unknown noise that can only be described in statistical terms, and $y_t$ is a known vector. If the state contains the positions of the inertial sensor module 102 of segments A and B, respectively, then $y_t$ is the three element vector describing the difference between the vectors d and c and $H=[I_3 -I_3]$. $I_3$ symbolizes the 3 by 3 identity matrix. Also, the state vector $x_t$ is obtained by integration of angular velocity and acceleration, as set forth in FIG. 2. A Kalman filter gives a weighted average between the state computed using the joint relation and the state computed using method in FIG. 2 according to a known Kalman update $x_{t,corrected} = x_t + K(y_t - Hx_t)$. In other words, the kinematics obtained according to FIG. 2 are corrected to conform to the joint relation. By continuously correcting the kinematics using the joint relation, unbounded integration drift is prevented.

The sensor fusion circuit 306 combines the biomechanical model constraints for the joint 302 with sensor signals from associated segments 300 and 304, to deduce a minimum error estimate of the states representing position, velocity, and orientation of segments and joints of the body 104. An example of a suitable algorithm for linear estimation of the states is described in T. Kailath, "Linear Estimation," Prentice Hall (2000), which is incorporated by reference in its entirety herein for everything that it teaches. In embodiments, the sensor fusion circuit 306 is a digital signal processor (DSP), such as a microcontroller, that implements a Kalman filter, a particle filter, or a similar estimation algorithm via hardware, firmware, software, or a combination thereof, to obtain estimates of the position, velocity, and orientation in light of the sensor noise. Suitable examples of DSP circuitry for implementing the fusion circuit 306 include the ADSP-BF531 Blackfin® processor manufactured by Analog Devices, Inc, as well as the Intel® Core™ 2 processor family manufactured by the Intel Corporation.

Other types of joint properties which can be used to improve motion tracking include biomechanical constraints in forces and torques. These constraints are obtained by kinematic calculations or inverse kinematics and require knowledge of masses of the associated body segments.

To minimize soft tissue or skin artifacts that occur when a sensor moves with respect to a bone of a given segment, the biomechanical model also employs the constraints in both position and rotation of specific joints. The artifacts occur when the observed position and rotation changes are physically unlikely. An example is shown in FIG. 5. If a rotation or position change of sensor 500 is measured that is not measured with sensor 504 and coincides with joint 502, it is likely due to a soft tissue artifact. Therefore, the data from sensor 500 is adjusted to fall within positional and rotational constraints for the joint 502. In one embodiment, the effect of skin artifacts is reduced by placing more than one sensor module on a single segment and weighting appropriately the individual sensor signals.

Since the human joint constraints and related sensor fusion algorithms are expandable to a complete body segment model, the sensor fusion circuit also estimates the positions and orientations of segments on which no sensor is attached. For example, in FIG. 1, the rotations of the neck vertebras 106 can be estimated using the orientation of the head 108 and the upper back 110 via the statistical modeling of the relationship between the different body segment motions.

Figure 6:
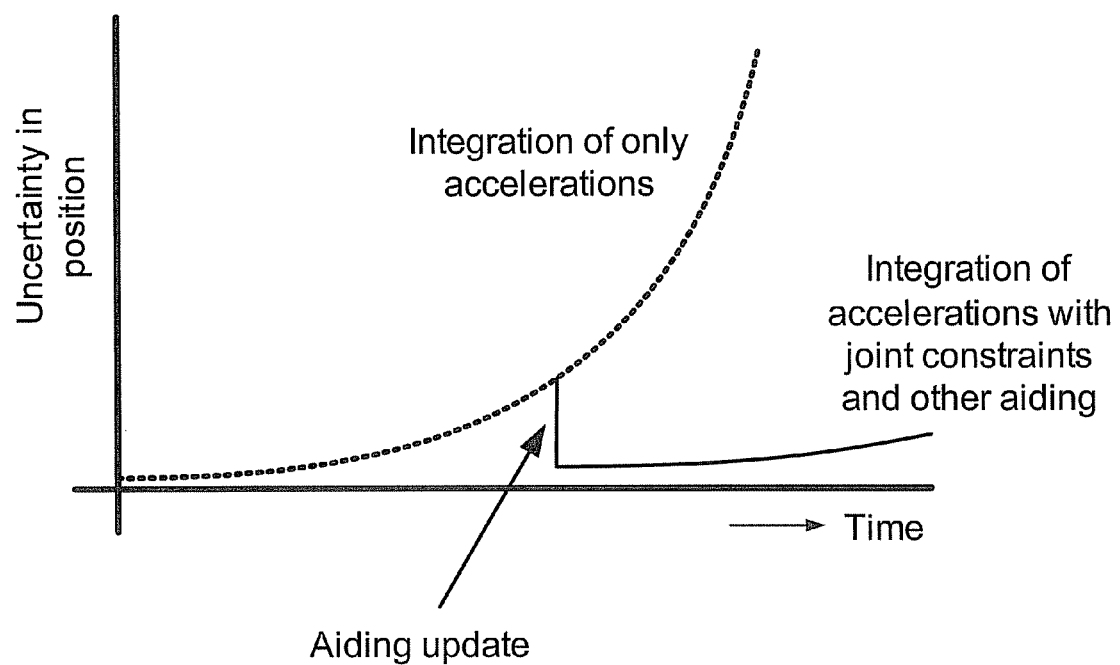
FIG. 6 is a chart illustrating the decreased uncertainty in estimation of position information when biomechanical joint constraints and aiding sensor information are used to estimate the moving subject's position.

In the presence of a gravity field, it can be assumed that the body must be in contact with an external physical world for the majority of the time due to the limited force generation capability of human beings. Hence, to minimize the 3D position drift of a complete computed body model with respect to a coordinate system not fixed on the body, the sensor fusion circuit also accepts an input indicating the detection of contacts of the body with its external surroundings. As illustrated in FIG. 6, by detection of an external contact, the uncertainty in position, especially in vertical direction, is minimized. It should be further noted that FIG. 6 applies to all measurement updates, including joint constraints and detection of external contacts. Therefore, uncertainty of the estimated position, velocity, and orientation data is reduced when measurement update information is taken into account.

Figure 7A:
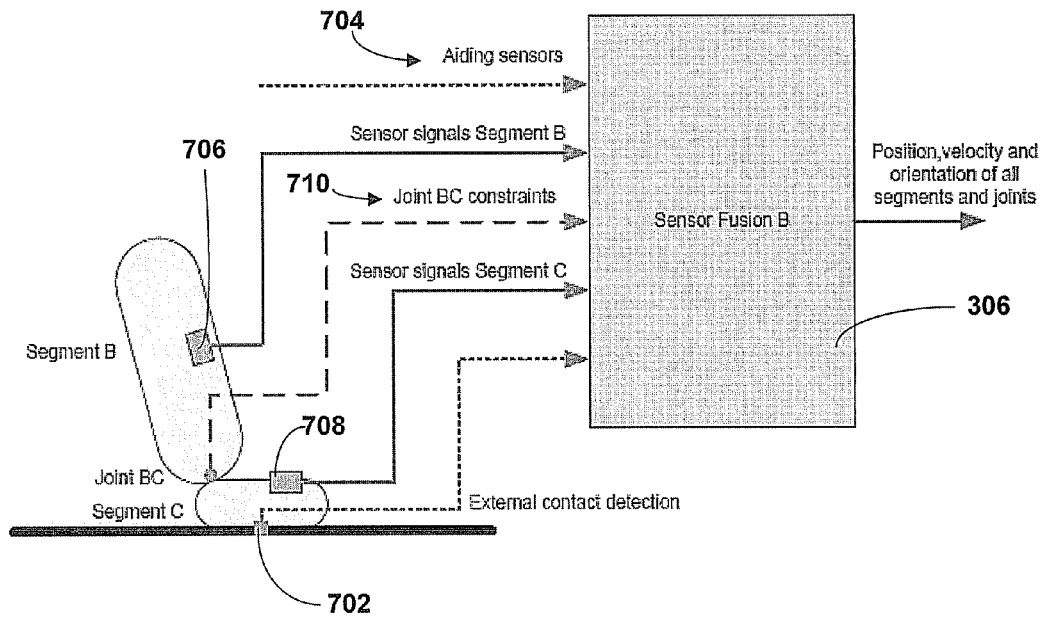
FIG. 7A is a schematic diagram of a centralized sensor fusion scheme that includes biomechanical joint constraints, external contact data, and other aiding sensor data for estimating the position, velocity, and orientation for all segments and joints, in accordance with an embodiment of the invention.
Figure 7B:
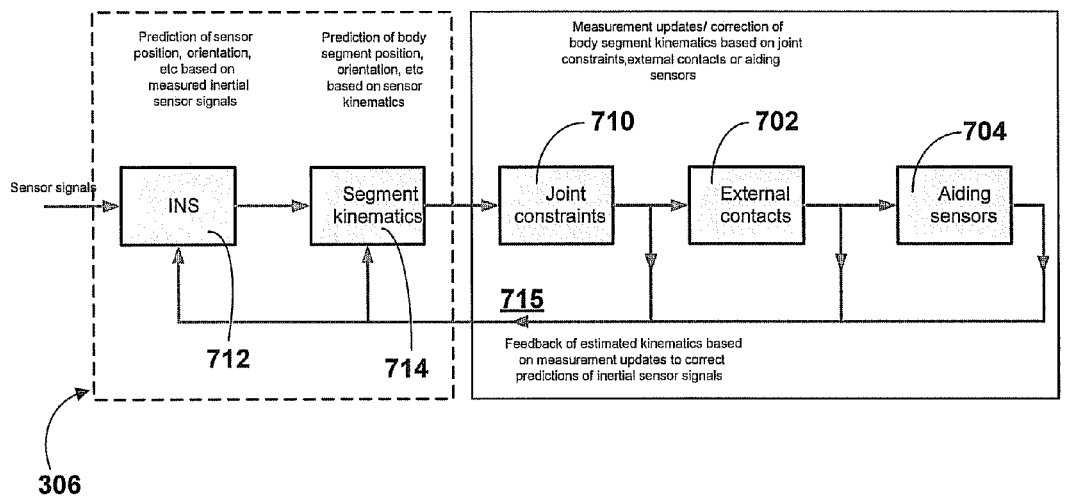
FIG. 7B is a schematic diagram illustrating the sensor fusion scheme of FIGS. 3 and 7A in more detail, in accordance with an embodiment of the invention.

As further illustrated in FIGS. 7A-7B, an embodiment of the sensor fusion circuit 306 combines the signals from inertial body sensors 706, 708 and aiding sensors 704 with the joint constraints 710 and external contact detection data 702, to estimate the position, velocity, and orientation of all connected body segments and joints. Preferably, detection of external contacts is performed without the use of contact sensors. In this case, detection of external contacts is based on computed kinematics, such as the position, velocity and acceleration, of relevant body segments. Other embodiments include improving the computed external contact detection data via an additional aiding sensor, such as a pressure sensor in the soles of the shoes, as part of an aiding sensor update 704 (FIG. 7B).

When external contact is detected, the sensor fusion circuit 306 updates the position and velocity estimates using one of the sensor fusion (estimation) algorithms discussed above in connection with FIG. 3. The sensor fusion circuit 306 employs a detailed anatomical model of the body, combined with modeling of the effect of a walking aid (e.g., a cane) and/or shoes, to detect external contacts by considering properties, such as position, velocity, and acceleration of relevant body parts and of the walking aid and/or shoes. In one embodiment, an external surroundings elevation map is incorporated into the external contact detection 702 to represent the interaction of the walking aid/shoes and/or body segments with the external world. Pressure or force sensors in shoes and in walking aids, are used to improve the contact detection. External contacts with the physical world can occur at any point of the human body and are not limited to feet touching the ground. Therefore, the fusion circuit 306 detects external contact at any probable body point, such as the hands on the floor, hands hanging on a bar, or the buttocks on a seat. The anatomical model employed by the fusion circuit 306 includes detection of deformation due to external contacts, such as by accounting for the soft tissue properties of the skin. In an embodiment, the anatomical model also incorporates friction properties of the contact surface, as well as of the skin and clothing or shoes. This approach also allows, for example, motion tracking on ice during skating or on snow during skiing.

Figure 7C:
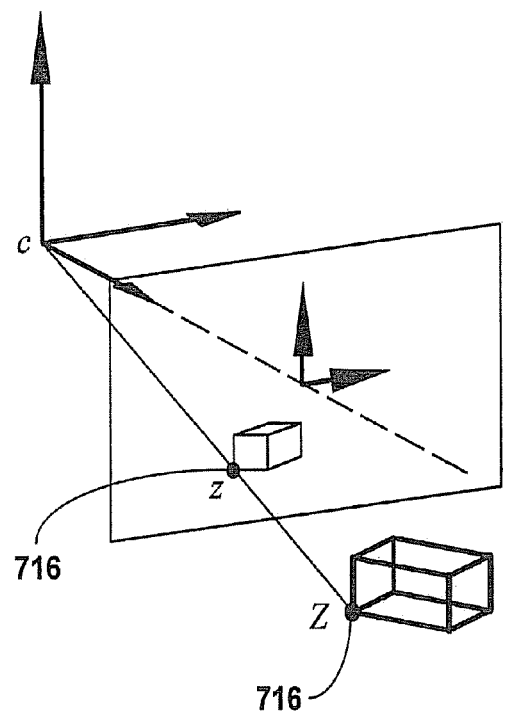
FIG. 7C is schematic diagram illustrating a 2D/3D correspondence associated with a camera aiding sensor for improving position estimates of an object, in accordance with an embodiment of the invention.

To further decrease the uncertainty of the position estimates, the sensor fusion circuit 306 accepts inputs from a variety of other aiding sensors 704, such as a GPS receiver, an RF-based local positioning circuitry, a barometer, a magnetic tracker (magnetometer), a camera, or other external sensors capable of relaying information with respect to the moving subject's surroundings. For example, when the aiding sensors 704 include a single camera, the position estimates are improved by evaluating the 2D/3D correspondences within the images. In an embodiment, the camera that is used to film the actor or object is used to improve the object's position and orientation estimate data by providing positional information of the object with respect to the environment. As illustrated in FIG. 7C, when a model feature 716 (point of interest on the subject) is detected in a camera image, a line exists relating the camera to the scene. This relation, referred to as 2D/3D correspondence, can be used to infer the position of the point of interest with respect to the camera. As related to a sequence of images, the displacement of the points of interest gives information about the position and velocity of this point. In an embodiment, this information is used as aiding information to update the position and orientation estimates obtained by integrating accelerations.

Even a 2D camera image from a single camera provides valuable positional information. The advantage of this approach is that the camera that is used to film the actor or subject is used to improve the actor's position and orientation estimate data by providing 2D positional information of the actor with respect to the environment. Preferably, a single camera provides sufficient position information correction/improvement since other kinematic data is retrieved from the inertial sensors. Additional embodiments include using a plurality of camera aiding sensors to obtain 3D positional aiding data.

Figure 7D:
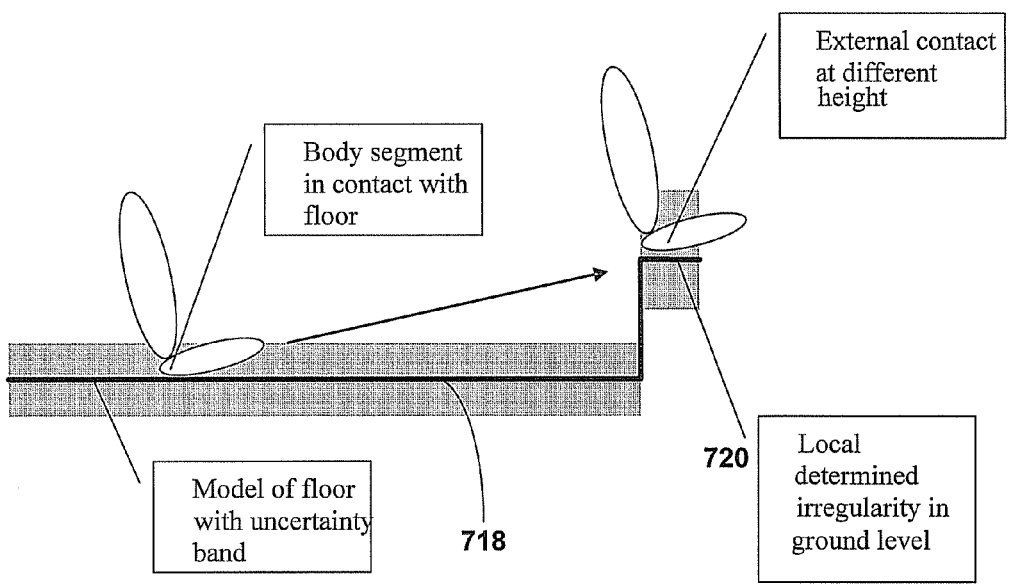
FIG. 7D is a schematic diagram illustrating an external surroundings model constructed using simultaneous localization and mapping (SLAM), in accordance with an embodiment of the invention.

In yet another embodiment, a map of the moving object's external surroundings is constructed within an unknown environment, while at the same time keeping track of the object's current position and orientation. This technique is called simultaneous localization and mapping (SLAM). In an embodiment illustrated in FIG. 7D, one of the assumptions of the external world model is that the ground 718 is flat with a predetermined uncertainty regarding its "flatness" to represent floor/ground irregularities. Alternatively, the model includes an elevation map comprising one or more predetermined irregularities 720 of the ground level 718. During motion tracking, the position of the body is updated based on the detection of external contacts. Thus, when an external contact is detected which does not fit within the uncertainty band (or is inconsistent with predetermined irregularities) of the ground model, the ground level is updated for the position at which the contact is detected and a complete elevation map is created. At the same time, when detecting an elevation which is already present in the constructed map, information about the location of the body is provided. In an embodiment, the additional positional information is used as an aiding sensor update 704 in the measurement update scheme of the fusion circuit 306 (FIGS. 7A, 7B).

Figure 7E:
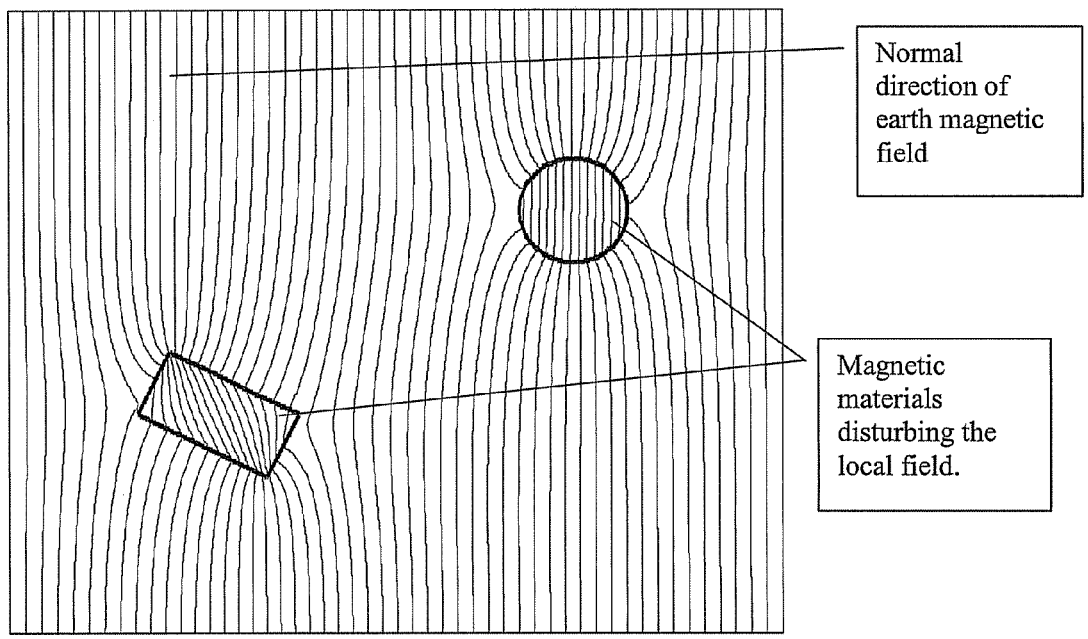
FIG. 7E is a schematic diagram illustrating the effect of magnetic materials on a local magnetic field.

An embodiment of the aiding sensors 704 includes a magnetometer, which serves as a compass to provide stability for rotations about the vertical axes. However the magnetic field can be distorted by nearby metal or magnetic materials (such as iron). Since the distortions in the magnetic field are strongly correlated in space, the magnetometers are distributed on the human body in order to track distortions in the magnetic field by combining the various (spatially distributed) measurements. This way, even a distorted field yields valuable information for full-body tracking. Using SLAM techniques, the properties of a disturbed field also provide positional information. As shown in FIG. 7E, a model of the earth magnetic field has a specified direction and magnitude, including predetermined uncertainties. Local disturbances yield specific place—magnetic field signatures/features. The mapping and detection of such disturbance signatures/features during tracking provides additional information, which is incorporated in the measurement update scheme as one of the aiding sensors 704.

In an embodiment where the aiding sensors include force sensing shoes, the sensor fusion circuit 306 also estimates the moving subject's center of mass and center of gravity. The force shoes include shoes having sensors under the heel and forefoot capable of collecting six degree-of-freedom force and moment (ground reaction force) measurements, as further described in Veltink et al., "Ambulatory Measurement of Ground Reaction Forces," IEEE Trans., Neural Systems (2005), which is incorporated herein by reference in its entirety for everything that it teaches.

Referring again to FIG. 7B, an embodiment of the sensor fusion circuit 306 is illustrated in further detail. The Inertial Navigation System (INS) module 712 processes the measured sensor signals to calculate the sensor kinematics, such as acceleration, velocity, position and orientation. The segment kinematics module 714, in turn, processes the calculated sensor kinematics to derive the body segment kinematics. This requires sensor-to-segment calibration to provide information on each sensor's position and orientation with respect to a corresponding body segment, knowledge of segment dimensions, as well as knowledge of where the sensor module is located on the segment. Further detail of the sensor-to-segment calibration process is disclosed in the incorporated European Patent Application No. EP07104283. For segments to which no sensor is attached, the fusion circuit 306 estimates the corresponding segment kinematics based on biomechanical relations between such segments.

The fusion circuit 306 employs a feedback arrangement 715 to correct the initial estimates of the sensor and body segment kinematics by updating these measurements with corresponding joint constraint, as well as external contact and aiding sensor data. While the depicted data flow of the measurement updates is illustrated as flowing from the joint constraints updates 710, followed by the external contacts updates 702 and updates from the aiding sensors 704, other measurement update data flow scenarios include a different order or combination of measurement updates. For example, the first update can come from the aiding sensors 704. Alternatively, the update from the aiding sensors 704 is not applied. Furthermore, the measurement updates can occur at different time intervals. For example, while the joint constraints 710 can be applied to every data sample coming from the INS/segment kinematics, the update from the aiding system 704 can be applied only once per second.

Figure 8:
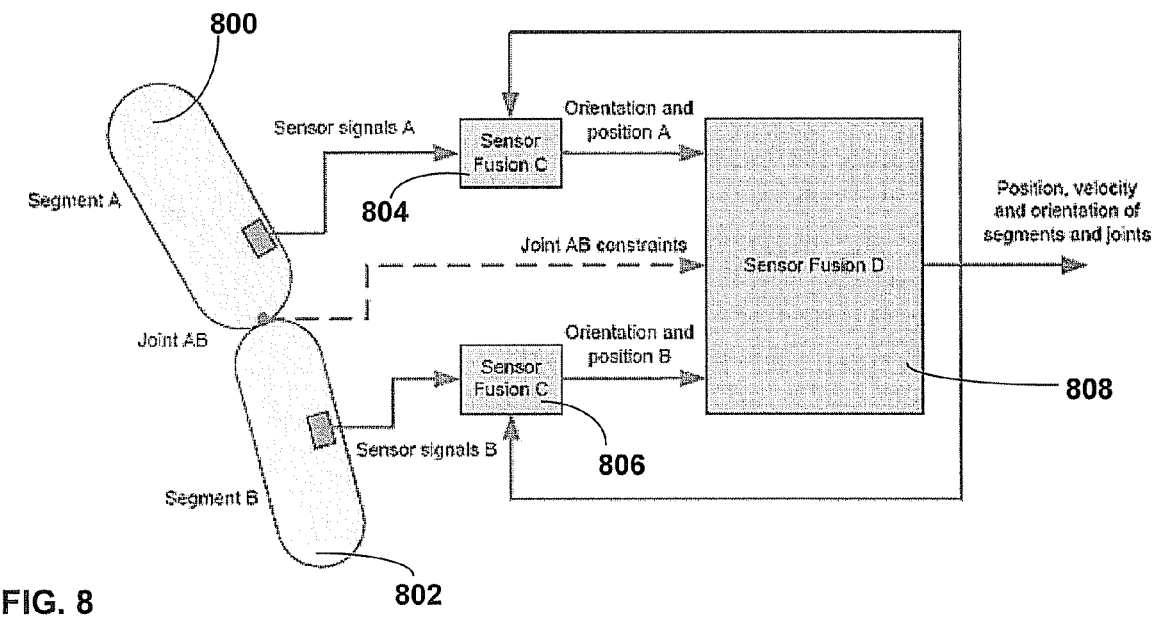
FIG. 8 is a schematic diagram of a decentralized sensor fusion scheme for estimating the position, velocity, and orientation information, in accordance with an embodiment of the invention.

The sensor fusion algorithm of the sensor fusion circuit 306 is not necessarily causal. It is possible to improve the estimation accuracy by combining the data from forward (real-time) and backward processing in time (e.g., RTS smoothing). In a centralized filter employed by the sensor fusion circuit of FIGS. 7A, 7B, all sensor signals and joint constraints are fused in one process. As illustrated in FIG. 8, other embodiments include using a decentralized filter scheme where the sensor signals from each individual body segment 800, 802 are first processed by its corresponding decentralized sensor fusion circuit 804, 806 to arrive at orientation and position estimates for each individual body segment 800, 802, after which the joint constraints and other measurement updates are applied via another sensor fusion circuit 808 and estimates of errors are fed back to each individual sensor fusion circuit 804, 806. To improve the position and orientation estimates, the external contact detection updates are applied to the decentralized sensor fusion circuits 804, 806, as well as to the sensor fusion circuit 808.

Figure 9:
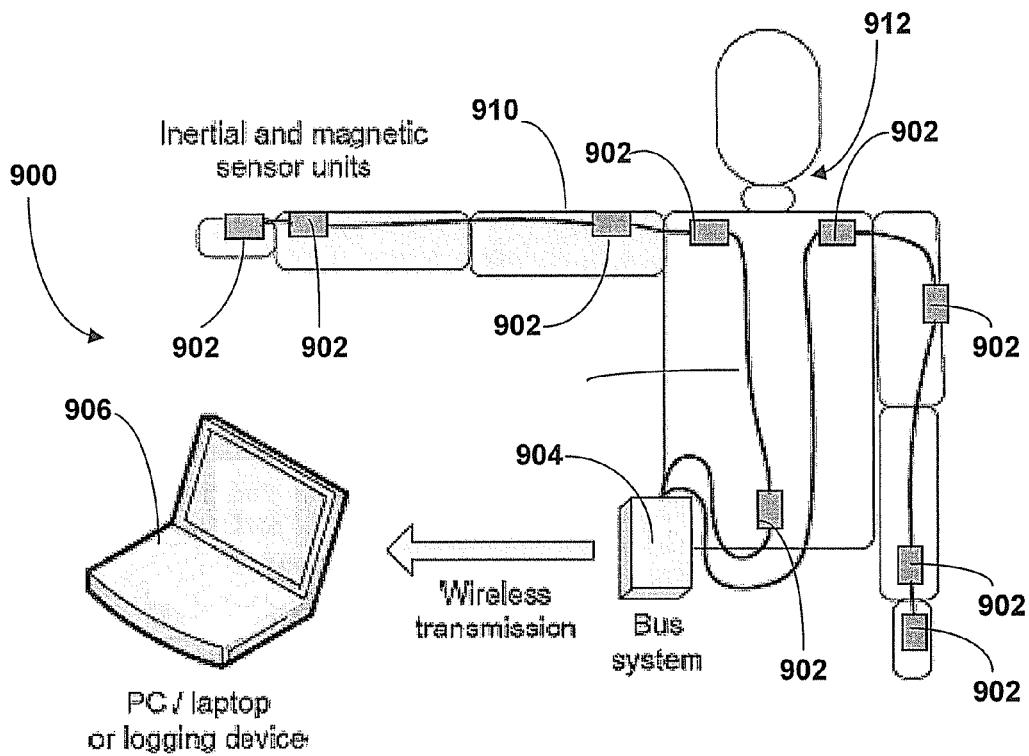
FIG. 9 is a schematic diagram illustrating an embodiment of a motion capture system employing wired body sensor modules.

Referring to FIG. 9, an embodiment of a motion capture system comprising a signal bus module for synchronization and wireless transmission of sensor signals is shown. The motion tracking system 900 includes a number of inertial and magnetic sensor modules 902 for each tracked body segment. The sensors 902 are connected to a bus module 904, which handles the power supply for all sensors, as well as synchronization of data sampling and wireless transmission of all sensor data and processed data to an external computer or logging device 906. The bus system contains one or more cables 908 for connecting the sensor modules 902. The cables and sensors are embedded in a suit 910, which fits tightly but comfortably to the skin of the moving subject 912. The suit 910 mechanically fixes the sensors 902 to the body and hides the associated cabling.

Figure 10:
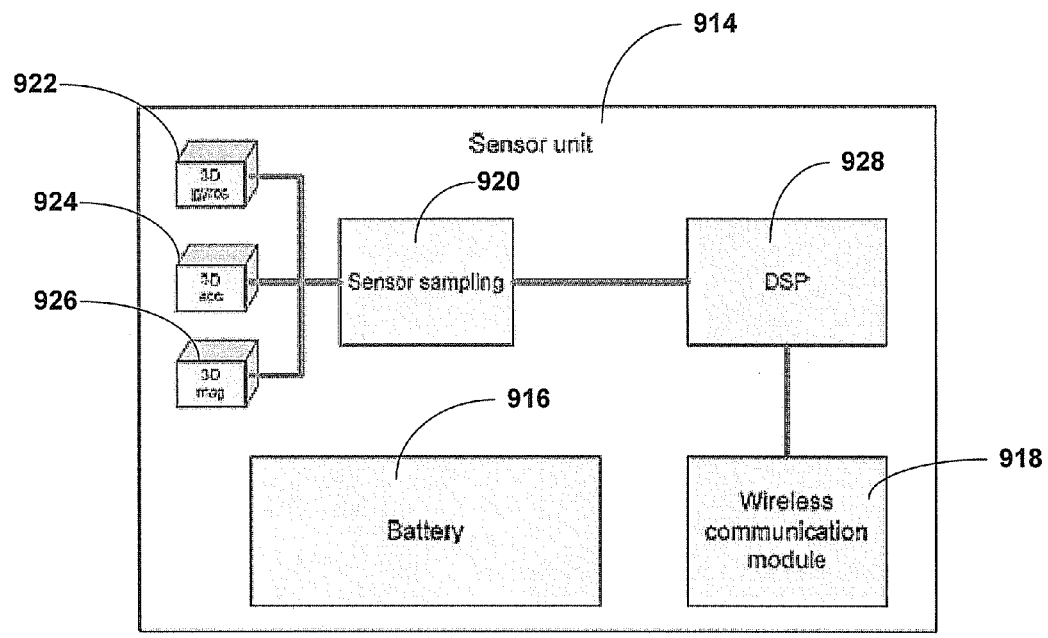
FIG. 10 is a schematic diagram of internal circuitry of a wireless body sensor modules, in accordance with an embodiment of the invention.
Figure 11:
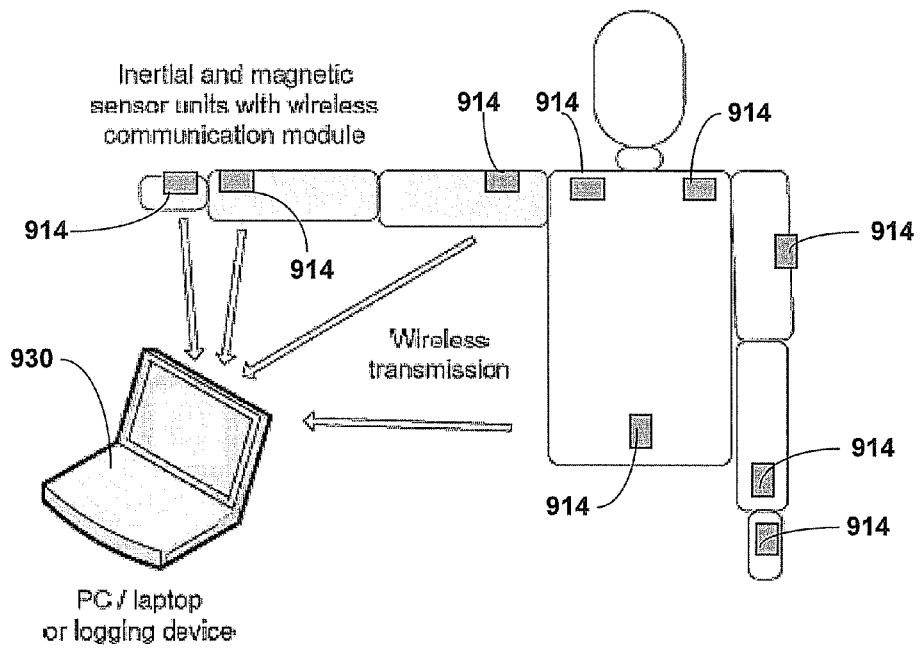
FIG. 11 is a schematic diagram illustrating a motion capture system employing wireless body sensor modules, in accordance with an embodiment of the invention.

In another embodiment illustrated in FIG. 10, to eliminate the use of cables 908 within the suit 910, each sensor 914 includes a battery 916 and a wireless communication module 918. In embodiments, the wireless communication module 918 employs Bluetooth, WiFi, UWB, or a similar wireless technology. The sensor sampling module 920 forwards the signals from each of the 3D gyro unit 922, 3D accelerometer unit 924, and 3D magnetometer unit 926 of the sensor unit 914 to the DSP module 928 for calculating the orientation and position estimates for the associated body segment. As further illustrated in FIG. 11, the wireless communication module 918, in turn, transmits the sensor data, as well as the calculated orientation and position estimates, to an external computer or logging device 930 for synchronization of sensor information between the sensors 914 and, optionally, additional processing of sensor data via a sensor fusion circuit described above in connection with FIG. 8, for example.

Exact synchronization between sensors achieves accurate registration of sensor data. When sampling at 100 Hz, for example, a timing error of 10 ms (1 sample) will result in an error of 10 degrees when a segment rotates at a rate of 1000 degrees/second, which is a likely angular velocity for the extremities of the body. In embodiments, a computer or external receiving device processes all sensor data using a centralized sensor fusion scheme described above in connection with FIGS. 7A, 7B. Alternatively, each sensor includes a digital signal processor (DSP) to execute a decentralized sensor fusion scheme as described above in connection with sensor fusion circuits 804, 806 of FIG. 8. In this case, an external computer/logging device, or, in case of a wired sensor suit, a processor in the bus module, applies the joint constraints and external contact constraints to the pre-processed sensor data.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for capturing motion of an object having a plurality of segments via a plurality of motion sensor modules located on the segments, each of two or more of the segments of the object having thereon at least one sensor module, each sensor module being adapted to capture 3D position data and 3D orientation data associated with its respective segment, the method comprising:
   collecting 3D inertial sensor data at each sensor module via at least one 3D accelerometer sensor and at least one 3D angular velocity sensor; and
   calculating a 3D orientation and 3D position of each segment having a sensor module by integrating the 3D angular velocity data and doubly integrating the 3D accelerometer data in time while applying a joint constraint to correct the calculated segment positions and orientations such that the segments are constrained to be linked to one another via a joint having at least one joint characteristic property, wherein applying the joint constraint is executed consistent with the at least one joint characteristic property and includes allowing a predetermined degree of laxity in one or more joints.

2. The method according to claim 1, wherein applying a joint constraint to correct the calculated segment positions and orientations further includes providing for two or more distinct biomechanical characteristics corresponding to two or more respective distinct joint types.

3. The method according to claim 1, further comprising updating the 3D orientation and 3D position calculation with one or more aiding sensors selected from the group consisting of a magnetic sensor, a GPS receiver, an RF-based local positioning sensor, a barometer, a pressure sensor, and a camera.

4. The method according to claim 3, wherein the one or more aiding sensors include a camera and the camera is adapted to improve the object's 3D position and 3D orientation calculation by providing at least 2D positional data of the object.

5. The method according to claim 1, further comprising updating the 3D orientation and 3D position calculation by detecting an external contact of the object with predetermined surroundings of the object based on at least one of position, velocity, and acceleration of one or more segments.

6. The method according to claim 1 wherein the object's surroundings are characterized by one or more predetermined assumptions, the method further comprising updating the one or more predetermined assumptions via a simultaneous localization and mapping technique.

7. A system for capturing motion of an object having a plurality of segments, the system comprising:
   a plurality of motion sensor modules including at least one sensor module located on each of two or more segments, each sensor module being adapted to capture 3D inertial sensor data; and
   at least one sensor fusion circuit for estimating 3D position and 3D orientation of the plurality of segments based on the 3D inertial sensor data captured by the motion sensor modules, and being adapted to apply a joint constraint to correct for drift by modeling the segments as being linked to one another via a joint having at least one joint characteristic property wherein the segment constraints comprise a biomechanical model of the object having a plurality of segment joints and allowing a predetermined degree of laxity in one or more joints.

8. The system of claim 7 wherein the at least one sensor fusion circuit estimates the 3D position and 3D orientation data via one of a Kalman filter and a particle filter.

9. The system of claim 7 wherein the biomechanical model of the object further accommodates distinct biomechanical characteristics corresponding to distinct joint types.

10. The system of claim 7 further comprising one or more aiding sensors for updating the 3D orientation and 3D position estimates for the plurality of segments, the aiding sensors selected from the group consisting of a magnetic sensor, a GPS receiver, an RF-based local positioning sensor, a barometer, a pressure sensor, and a camera.

11. The system of claim 10 wherein the one or more aiding sensors include a camera and wherein the camera is adapted to improve the body's position estimate by providing positional information associated with the body's environment.

12. The system of claim 7 further comprising a logging device adapted to provide synchronization of information between the sensor modules and to provide further processing of sensor data via the at least one sensor fusion circuit.

13. A motion sensor module for capturing motion of at least one of a plurality of object segments, wherein the motion sensor module is located on the at least one of the segments, the motion sensor module comprising:

at least one of a 3D accelerometer sensor and a 3D angular velocity sensor for collecting 3D inertial sensor data associated with the at least one segment; and a sensor fusion circuit for estimating 3D position and 3D orientation data based on the 3D inertial sensor data, wherein the sensor fusion circuit updates the 3D position and 3D orientation estimates by applying a plurality of joint constraints based on predetermined characteristics of the object segments to correct for drift by modeling the segments as being linked to one another via a joint having at least one joint characteristic property, allowing a predetermined degree of laxity in one or more joints.

14. The motion sensor module of claim 13, wherein the model further provides for distinct biomechanical characteristics corresponding to distinct joint types.

15. The motion sensor module of claim 13 wherein the sensor fusion circuit estimates the 3D position and 3D orientation data via one of a Kalman filter and a particle filter.

* * * * *